United States Patent [19]

Larsen

[11] Patent Number: 5,027,829
[45] Date of Patent: Jul. 2, 1991

[54] APPARATUS FOR DIATHERMY TREATMENT AND CONTROL

[76] Inventor: Lawrence E. Larsen, 308 Hamilton Ave., Silver Spring, Md. 20901

[21] Appl. No.: 369,200

[22] Filed: Jun. 21, 1989

Related U.S. Application Data

[63] Continuation-in-part of Ser. No. 941,649, Dec. 15, 1986, Pat. No. 4,848,362.

[51] Int. Cl.$^5$ ............................................. A61N 5/02
[52] U.S. Cl. ............................. 128/804; 219/10.55 F
[58] Field of Search ..................... 128/804, 422, 421; 219/10.55 R, 10.55 F, 10.55 A

[56] References Cited

U.S. PATENT DOCUMENTS

| | | | |
|---|---|---|---|
| 3,065,752 | 11/1962 | Potzl | 128/804 |
| 4,108,147 | 8/1978 | Kantor | 128/804 |
| 4,312,364 | 1/1982 | Convert | 128/804 |
| 4,332,260 | 6/1982 | Bicker | 128/804 |
| 4,341,227 | 7/1982 | Turner | 128/804 |
| 4,409,993 | 10/1983 | Furihata | 128/784 |
| 4,446,874 | 5/1984 | Vaquine | 219/10.55 F |
| 4,528,991 | 7/1985 | Dittmar et al. | 128/804 |
| 4,556,051 | 12/1985 | Maurer | 128/421 |
| 4,709,701 | 12/1987 | Weber | 128/804 X |
| 4,848,362 | 7/1989 | Larsen | 128/804 |

OTHER PUBLICATIONS

Guy et al., IEEE Trans. Microwave Theory and Tech. MIT-26(8): 550-556, 1978.

*Primary Examiner*—Lee S. Cohen
*Attorney, Agent, or Firm*—Laubscher, Presta & Laubscher

[57] ABSTRACT

A method and apparatus for therapeutic deep heating of musculoskeletal tissues are characterized by an improved transducer that serves simultaneously to couple the power from the generator into the patient and to sense the therapeutic response for treatment control including a method of manufacture and testing of contact applicators for dielectric heating of musculoskeletal tissue. The applicator is comprised of a rectangular wave guide in which the location of the dielectric material is adjusted to reduce the measured value of the guide wave length to the free-space value at the frequency of operation. In addition, the invention comprises a method and apparatus for the noninvasive detection of therapeutic response in tissue to dielectric heating. This response is then used to control the treatment. Both heating and sensing are accomplished by one transducer and one apparatus if dielectric heating is employed. If other forms of heating are used, such as ultrasound, the sensor still occurs but the apparatus must be modified, the modification including replacement of the high power electromagnetic source with a low power source version.

9 Claims, 11 Drawing Sheets

APPARATUS FOR DIATHERMY TREATMENT AND CONTROL

This application is a continuation-in-part of prior U.S. application Ser. No. 941,649 filed Dec. 15, 1986, U.S. Pat. No. 4,848,362.

BACKGROUND OF THE INVENTION

The present invention relates to a transducer and apparatus for deep heat therapy in the treatment of musculoskeletal disorders, and more particularly to a low leakage radio frequency (RF) contact applicator design with skin and subcutaneous cooling, methods of applicator manufacturing, including applicator testing for quality assurance, as well as methods for detection of therapeutic response to achieve treatment control that may use the same transducer simultaneously for effector and sensor functions. Improved electronics for the apparatus and new radome and bolus designs are also disclosed.

BRIEF DESCRIPTION OF THE PRIOR ART

That dielectric heating of musculoskeletal tissue is more efficacious and more efficiently accomplished by contact applicators was established by Kantor as shown in U.S. Pat. No. 4,108,147.

Subsequent improvements deal with broad band tuning to accomplish efficient transfer of microwave energy from an applicator into tissue over a wide band of frequencies, and cooling using air as well as water, or convective as well as conductive as disclosed in the Turner U.S. Pat. No. 4,341,227.

A slotted, metallic cover over the radiating aperture of a waveguide applicator is the subject of the Potzl U.S. Pat. No. 3,065,752.

The Vaguine U.S. Pat. No. 4,446,874 discloses coupling and tuning involving decoupling input coupling of the magnetic loop, whereby the frequency of operation and input match are adjusted.

The Weber U.S. Pat. No. 4,709,701 discloses a method for automatic tuning of a hyperthermia apparatus.

The design procedures cited in the Kantor patent are not viable because these procedures did not provide for compensation and control of evanescent modes in the waveguide applicator. These modes exist principally in the area of the feed that couples microwave energy from the generator via a coaxial cable into the applicator, and on into the patient.

As a result of these modes, the guide wavelength is not equal to the free space wavelength at the frequency of operation, i.e., the TEM mode referred to by Kantor is not necessarily established. The TEM mode cannot exist in a hollow tube waveguide; nevertheless, uniformity of the electric field across the aperture can be improved when the guide wave length is shortened to that of the free space by the use of partial filling with dielectric material parallel to the narrow wall of the guide.

The reduction of guide wavelength to the free space value is, therefore, a necessary, but not a sufficient condition to accomplish more nearly uniform electric fields across the aperture. Although the guide wavelength may also be shortened by partial filling by dielectric parallel to the broad wall, this does not yield the uniform electric field distribution across the aperture.

The instant invention shows that the length of the dielectric material in the waveguide applicator must also be an appreciable fraction of a wavelength in order to establish the desired guide wavelength and provides for confirmation of the guide wavelength and methods of quality assurance exist in the prior art.

Additionally, this invention establishes the relationship between aperture electric field distribution, guide wavelength, and specific absorption rates at depth sites, none of which is provided for by the prior art.

The instant invention also improves air cooling methods of prior designs which were wholey or partly non-contacting in order to allow egress of air over the patient's skin. The necessary spacing promoted RF leakage as well as tuning variation as the air gap varied with breathing or other motions. RF leakage was not controlled at the point of air ingress and the simple propeller fan mounted within the applicator of the prior design introduces undesirable vibration that modulates the match by alteration of the air gap.

The invention provides a method for detection of therapeutic response to control dielectric heating during the treatment. Until this invention, no specific individual treatment response has been possible. Prior art was subjective, and at best, the manufacturer provided tabled standards of power and duration for the general population which failed to accommodate for the variations between individuals and were no more than general recommendations. The instant invention makes use of the increase in local blood flow and blood content in muscle consequent to local temperature elevation and the consequent wave impedance change due to the change in tissue electrical properties, i.e., the instant invention both provokes and detects reactive hyperemia which is the therapeutic response.

The technology of combined microwave heating with sensing has been recognized in other areas. The Furihata U.S. Pat. No. 4,409,993 addressed the need to control dose in an endoscopic device that uses microwave power to heat cancerous tissue to the point of eschar as verified by optical visualization of necrosis. The Converse U.S. Pat. No. 4,312,364 and its progeny use microwave radiometry to sense heating from an exogenous microwave source.

The instant invention uniquely provides for both heating and sensing of the therapeutic response through the dual use of an antenna. No prior art utilizes the combined effector/sensor action of the instant invention, using the change in complex permittivity of the target tissue due to local vasodilation, nor were the prior methods based on a closely coupled antenna, whereby antenna impedance alterations are used to infer changes in the wave impedance of the tissue secondary to the desired reactive hyperemia. Prior technology did not use the critical guide wavelength, design methods, a radome, or surface cooling incorporated as with the instant invention.

Heretofore, cooling of the treatment site was accomplished either by air flow over the site, i.e. convection cooling as disclosed by the U.S. patents to Vaguine U.S. Pat. No. 4,446,874 and Becker U.S. Pat. No. 4,332,260 and by A. W. Guy et al in IEEE Trans. Microwave Theory and Tech., MTT-26(8): 550–556, 1978, or by the use of a water filled applicator or a water blanket within which chilled water is circulated as disclosed in the U.S. patent to Dittmar U.S. Pat. No. 4,528,991.

The present invention uses a heat sink produced by chilled air circulated to the applicator, whereby the treatment site is cooled by thermal conduction through the radome (which is in contact with the treatment site) to the applicator.

The radome is both a thermal and electromagnetic interface. With respect to the former, it is an interface between heat sources induced at the treatment site and the heat sink provided by chilled air cooling of the entire applicator. Thus a thermal gradient is created across the radome. The radome not only covers the aperture to prevent fringe field heating, but is also the heat conduction path between the heat sources in the treatment site and the heat sink produced in the applicator.

Clinical studies confirm the need for a radome to prevent fringe field heating in human subjects. While the prior devices (i.e. Guy) prevent fringe field heating, they have the following deficiencies: (1) because air ducts are part of the radome structure, the radome suffers RF leakage in excess of FDA guidelines; (2) the acrylic material from which the radome is constructed does not match that of skin or sub Q fat, whereby scattering is increased. Dielectric losses in the material in combination with its thickness lead to significant heating of the radome. Clinical studies show a bar-like pattern of erythema on the subject's skin caused by the combination of heating and loss of cooling at the sites corresponding to the walls of the air ducts. (3) The air flow that could be accommodated by the miniature air ducts enclosed in the radome is too low to remove heat from the radome itself when the RF power is on.

The radome of the present invention was developed in order to overcome these and other deficiencies of the prior art. Rather than blow air on the surface of the skin, heat is transferred through the thermal conductivity of the radome to a heat sink located in the waveguide.

Conventional bolus materials are water based solutions encased in a bladder as disclosed for example in the Dittmar U.S. Pat. No. 4,528,991. Water based materials have a dielectric constant much higher than fat/skin at the treatment site interface. Attempts to vary the dielectric constant and loss tangent by means of polysaccharides (e.g. Dextran) dissolved in water produce a final value of $k'=62$ to 67, whereas the $k'$ of skin/fat is in the range 3 to 6. As a result, scattering and stray fields are increased. Further, the high dielectric loss of water reduces the efficiency of power transmission. Typical values of the loss tangent for the bolus material of the prior art is in the range 0.42 to 0.45.

The instant invention uses ceramic spheres of final dielectric constant near fat/skin, whereby stray fields are reduced and power transfer efficiency is increased. Further, the air/ceramic bolus provides very low loss wherein the loss tangent is less than 0.05.

SUMMARY OF THE INVENTION

This invention provides new, improved treatment apparatus for dielectric heating as a therapy for musculoskeletal disorders. Implemented are improved methods for contact applicator design which produce more uniform heating in the transverse plane, greater depth of microwave penetration, and apparatus construction which can utilize a dual role of the transducer for both application of power as well as a transducer for sensing the therapeutic response during the treatment without interruption of power delivery.

Quality assurance methods are provided including methods for guide wavelength verification, input match as a function of frequency as well as guide wavelength, and air cooling of the skin which has eliminated spaced applicators and does not promote RF leakage.

A thin radome with a dielectric constant approximately that of subcutaneous fat is employed to interface the applicator to the patient. The radome serves to both prevent fringe field coupling to the patient (leading to excessive heating at the narrow walls of the wave guide where they would otherwise contact the patient), and to provide a low thermal impedance between the air cooling that heat sinks its inner surface and the patient's skin that is in contact with its outer surface. The radome according to the invention achieves high thermal conductivity with significantly reduced RF leakage and improved skin cooling while fringe field effects are prevented.

The invention provides for use of the applicator additionally as a sensor for detection of therapeutic response, and use of the sensor response to control the dielectric heating treatment on an individual basis. This is accomplished by measurement and control of the net power absorbed at a level sufficient to produce the desired therapeutic response of increased muscle blood flow. The increased muscle blood flow is a reactive hyperemia in response to temperature elevation. Local temperature elevation in the muscle provokes local vasodilation, opening capillary beds and arterioles. The desired therapeutic response is this reactive hyperemia, i.e., increased local blood flow and blood content which promotes, for example, resolution of inflammatory infiltrates. The detection of reactive hyperemia also provides an indirect and qualitative measure of muscle temperature in the pattern of the applicator since the local vascular response is triggered at temperatures near 40 degrees centigrade.

According to a primary object of the invention, improved source and processor electronics are provided. More particularly, the power source is a stabilized oscillator, and a complex ratiometer is used for indicating a complex scattering parameter resulting from changes in wave impedance due to blood flow and blood content of the tissue being treated.

The ratiometer includes an in-phase in-quadrature network for receiving both a sample of the power wave applied to the tissue and a sample of the power wave reflected therefrom to produce outputs proportional to the phase angle between the two power signals.

According to another object of the invention, a therapeutic response processor is connected with the complex ratiometer for detecting the time rate of change of the phase angle during treatment. A differential angle processor produces an output which is an absolute value of the difference between instant and stored values of the phase angle of the scattering parameter in radian base, parallel binary form.

Another object of the invention is to provide an improved bolus for use with the apparatus. The bolus includes a flexible pouch and a mixture of air and a plurality of spherical ceramic bodies arranged therein. The bodies are formed of low loss material, whereby the mixture has a dielectric constant in the range of 3-5 to provide efficient power transmission between the treatment apparatus and a patient.

BRIEF DESCRIPTION OF THE FIGURES

Other objects and advantages of the invention will become apparent from a study of the following specification when viewed in the light of the accompanying drawing, in which.

DETAILED DESCRIPTION

Figure 1:
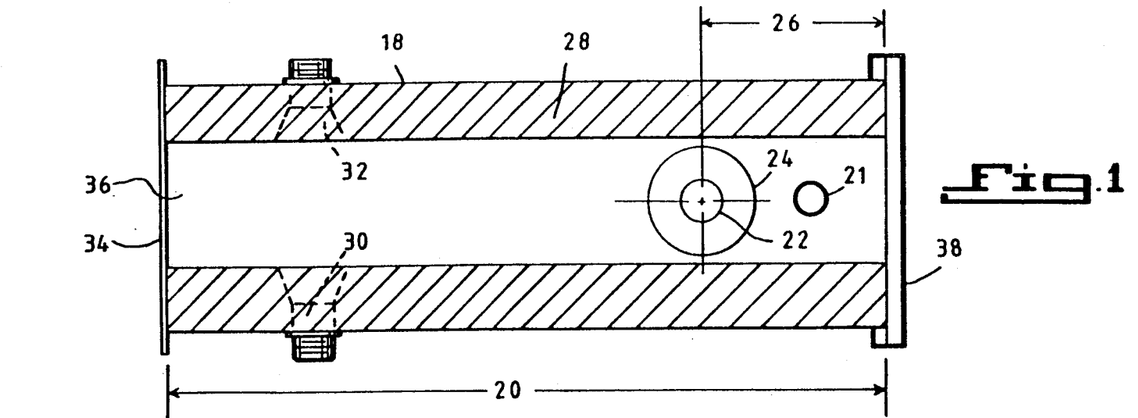
FIGS. 1, 2 and 3 are the top, side and end orthographic projections, respectively, of one configuration of a preferred embodiment of the invention for an applicator/sensor showing a monopole type of electric field feed as the coax to waveguide adapter.
Figure 2:
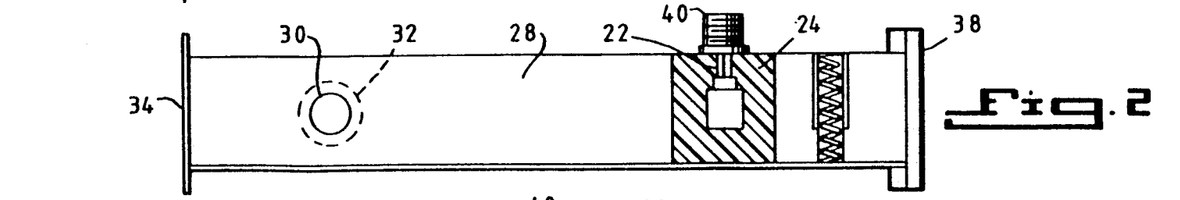
Figure 3:
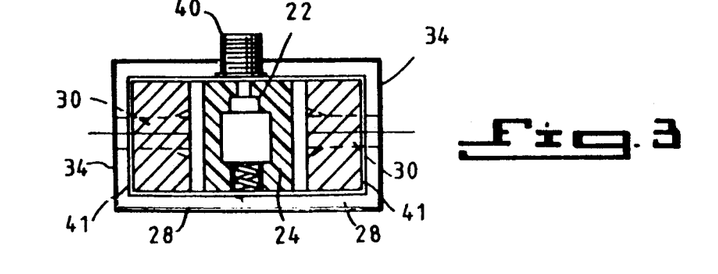

Referring to the drawings, FIGS. 1, 2 and 3 generally depict an applicator 18 of length 20, to be substantially equal to one wavelength at the free space phase velocity, an electric field feed 22, encased in a polystyrene cylinder 24, placed at a distance 26 of one quarter of the guide wavelength (previously established to be equal to the free space wavelength at the frequency of operation).

The high dielectric constant ($k'=10$) and low loss (tan $\delta=0.0002$) ceramic ($>96\%$ $Al_2O_3$) material 28 is placed against the narrow walls of the waveguide 36 and held by mechanical fasteners 30 to the narrow wall. The access to the mechanical fixation on the inside of the applicator is closed by a ceramic plug 32 of substantially the same dielectric properties as material 28, and a thin, e.g. 0.030", radome 34 fabricated from high thermal conductivity material such as Kapton or composite (e.g. G10 with a $k'=4$) and oriented such that the fiber is cross polarized to the electric field in the waveguide 36.

The input match is tuned by means of the depth of penetration of the cylindrical feed 22 into the waveguide 36. An optional spring loaded inductive post tuning device 21 is placed between the feed 22 and the short circuit 38.

There is a connector 40 for the coax cable transmission line from the generator. Only coarse tuning to a return loss of less than 10 db is effected by use of the tuning device 21 with the radome 34 of the applicator being in contact with simulated fat and muscle phantom prepared according to the methods of prior art. A selected gap is produced by low loss dielectric shims 41.

Provision for tuning the input impedance to the source are also shown in FIGS. 1, 2 and 3. The thickness of the longitudinal dielectric material is selected to produce a longer than critical guide wavelength in a test fixture. Small adjustments in the guide wavelength are made by the insertion of low loss shims 41 between the narrow wall and the dielectric to shorten the guide wavelength.

Figure 4:
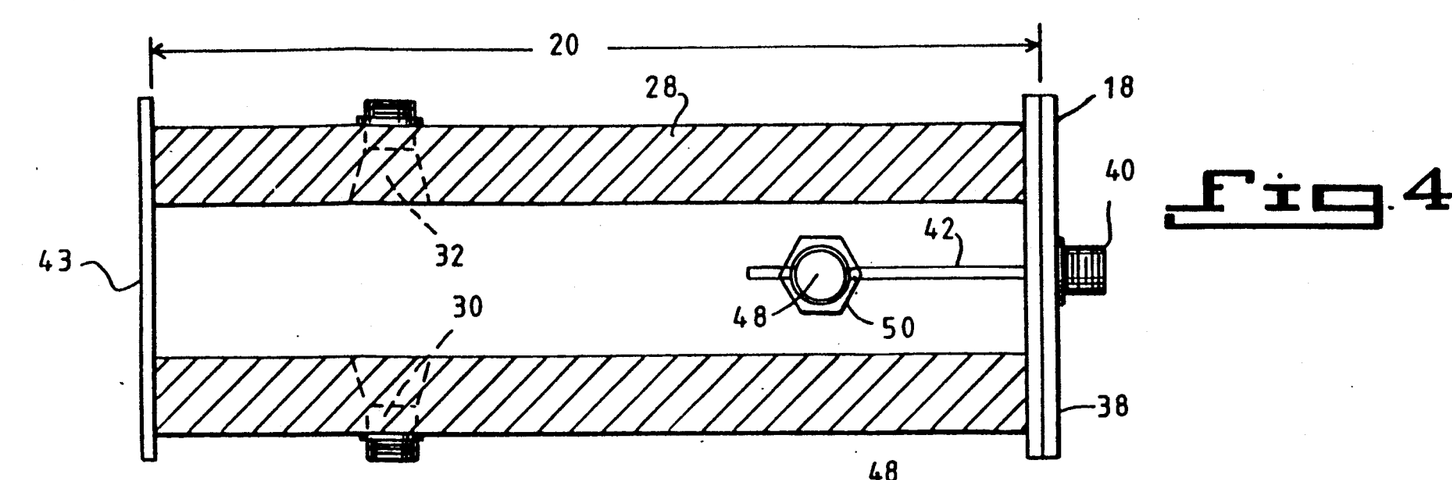
FIGS. 4 and 5 are top and side orthographic projections, respectively, analogous to FIGS. 1 and 2 above, of another embodiment using a magnetic field feed in the form of a shorted loop.
Figure 5:
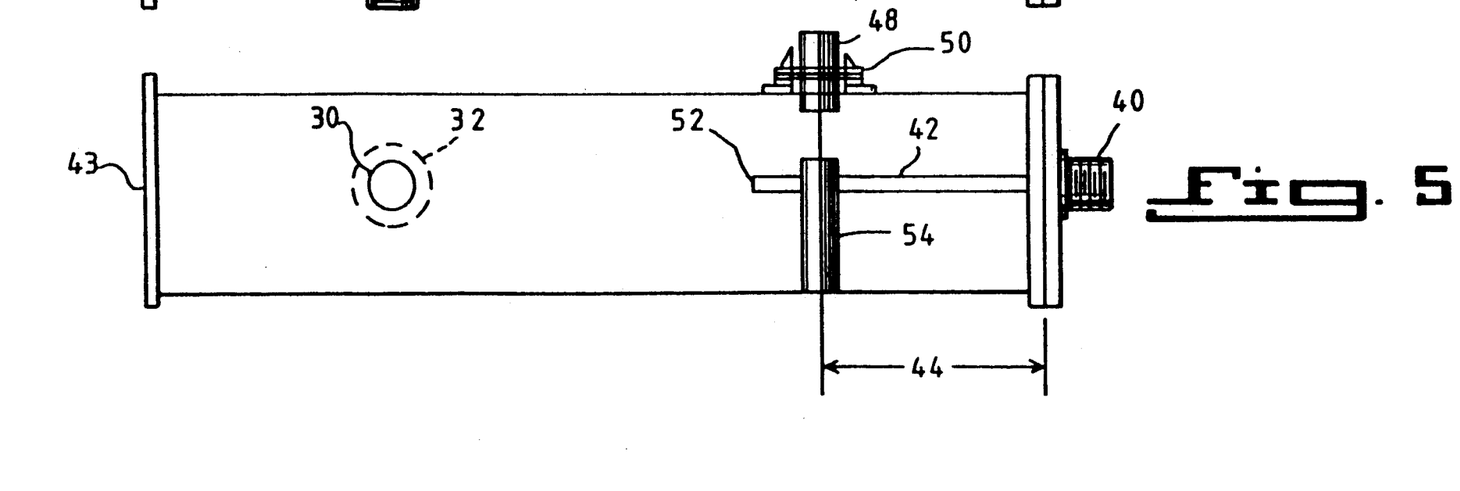

A second embodiment is shown in FIGS. 4 and 5 which are the top and right side orthographic projections analogous to FIGS. 1 and 2 above. The length 20 of the applicator 18 and dielectric material 28 is substantially one wavelength at the free space phase velocity. The feed 42 is a magnetic loop shorted at a quarter guide wavelength 44. It is tuned for input impedance by a capacitive shaft 48 and shaft lock 50.

This is preferable to a tuning screw since the shaft lock 50 is a collet and clamp that makes more reproducible RF ground than a jamb nut and screw. Another degree of tuning is provided by a stub 52 extending from the post 54. Only coarse tuning to a return loss less than 10 db is effected by use of the tuning device with simulated fat and muscle against the radome 34.

Figure 6:
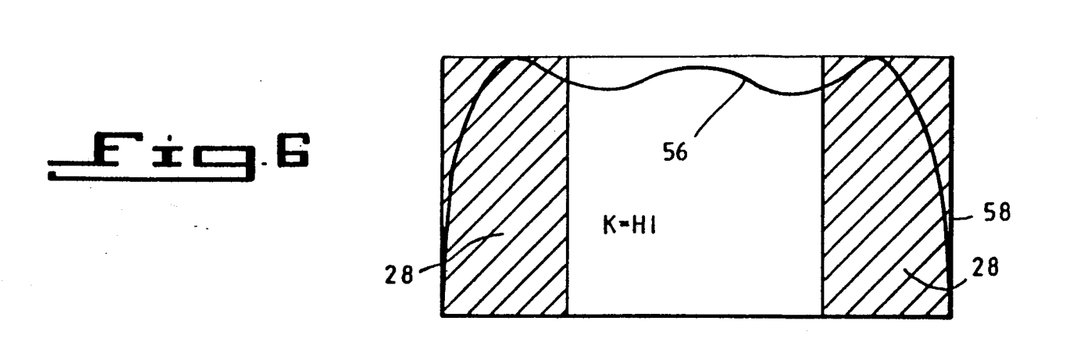
FIGS. 6, 7 and 8 illustrate a high dielectric constant (above critical value), the critical value dielectric constant, and a low dielectric constant, respectively, in diagramatic views of the waveguide showing the expected electric field distribution in the dielectric material and air filled portion of the waveguide.
Figure 7:
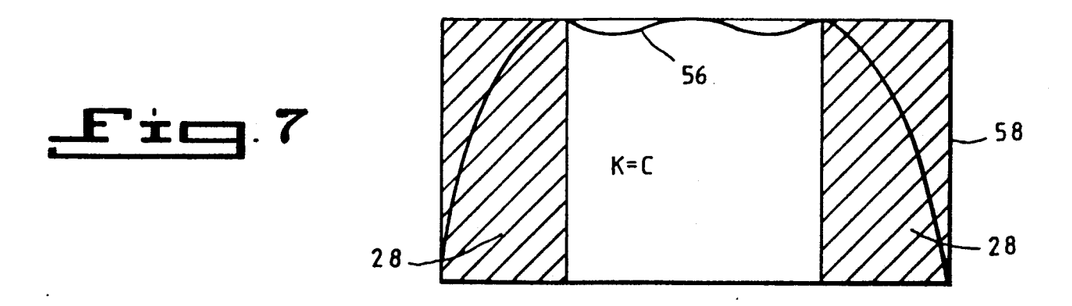
Figure 8:
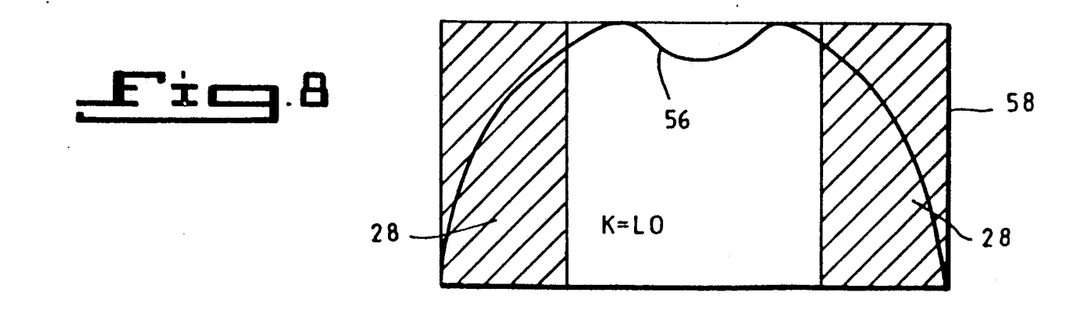

FIGS. 6, 7, and 8 illustrate the conditions of guide wavelength shorter than the critical value, that for the critical value (the free space value), and guide wavelength longer than the critical value, respectively and represent the electric field distribution 56 in the transverse E plane of guide 58. As shown in FIG. 8, the electric field peak is outside of the dielectric material and in the air filled region of the guide. The critical condition shown in FIG. 7 is also the one where specific absorbtion rates (SAR) are highest at distances in the order of 1 to 3 cm below the fat-muscle interface.

The dielectric material 28 is shown in apposition to the narrow wall of the applicator 18 and of equal thickness, but of three values of dielectric constant (high, critical and low) for purposes of illustration.

The electric field distribution 56 in the transverse plane is effected by the guide wavelength as the latter relates to the critical value. When the dielectric material 28 decreases the phase velocity excessively, in comparison to a guide completely filled with air, it may produce a guide wavelength that is too short and the electric field peak exists inside the dielectric as shown in FIG. 6. If the dielectric material 28 does not sufficiently contract the guide wavelength, i.e., the guide wavelength is too long, then the peak occurs in the air filled portion of the guide as shown in FIG. 8. At the critical guide wavelength, the peak is just inside the dielectric at the air interface as shown in FIG. 7.

Figure 9:
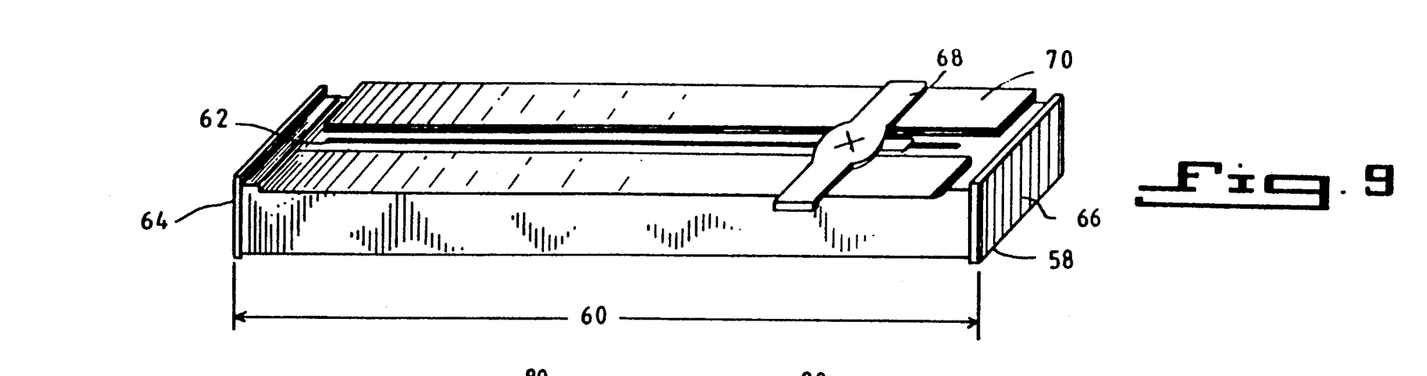
FIGS. 9 and 10 are a perspective and end projection, respectively, of one configuration of a preferred embodiment of the invention which is used for manufacturing quality assurance, e.g., to establish the guide wavelength at the critical value.
Figure 10:
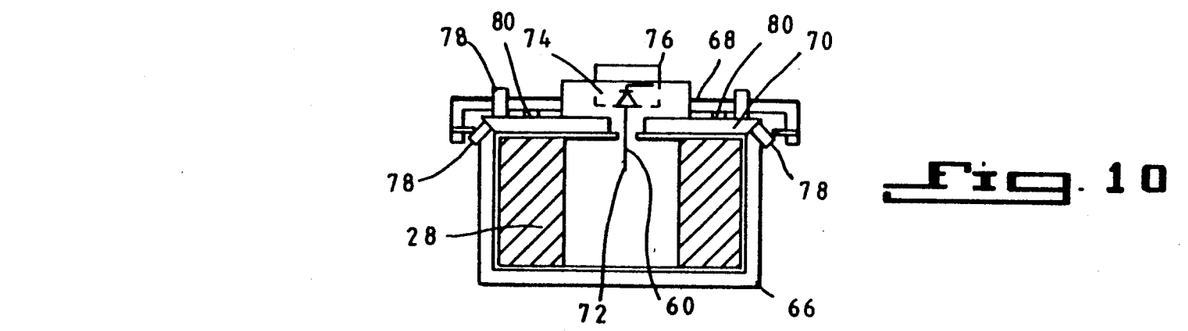
Figure 11:
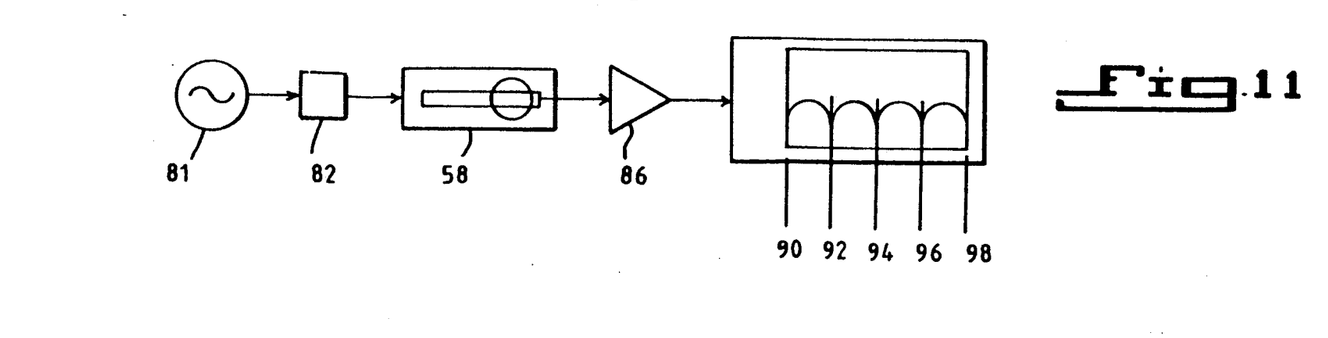
FIG. 11 is a functional block diagram of the quality assurance apparatus.

A third embodiment is shown in FIGS. 9 and 10 which is the apparatus used with the method for assuring manufacturing quality and optimizing applicator operation. This is composed of a waveguide applicator of twice normal length, shorted at both ends to establish a standing wave, and with a movable carriage/probe to sample the electric field distribution via a narrow slot in the center of the guide as shown in FIG. 9. The test fixture guide has transverse dimensions equal to the applicator and contains the same feed and dielectric material as shown in either of the first two preferred embodiments. The electric field feed, for example, and carriage shown in FIG. 11 illustrates typical results as well as the selected node-to-node distance.

FIG. 9 shows a test fixture 50 of length 60, twice the length of the applicator, with a narrow slot 62, milled into one broad wall. The test fixture 58 is fitted with dielectric of the same thickness and constitutive properties as that used in the applicator.

The waveguide test fixture interior dimensions are also identical to the applicator 18 in the transverse plane. The feed is placed at the shorted proximal end 64 whereas the distal end 66 is terminated to produce an electric standing wave pattern as shown in FIG. 11. The standing wave pattern is measured by a carriage assembly 68 that is scanned along a track 70 on either side of the slot 62.

The carriage assembly 68 holds a probe 72 connected to a variable line stretcher 74 and thence to a crystal diode detector 76. The carriage runs on the two piece track 70 by means of conductive wheels 78 and spring contacts 80. This permits scanning the probe 72, at an adjustable, but minimal penetration, over a large fraction of the length of the test fixture 58.

FIG. 11 shows a signal source 81, a low pass filter 82, with a cut-off 10% above the frequency of operation, and the test fixture 58 shown schematically. The feed energized in the test fixture 58 is also identical to that used in the applicator 18. The RF drive produced by the signal source 81 is square wave modulated at an audio frequency and the detector output is amplified by a tuned amplifier 86.

A typical pattern of electric field standing waves is shown as a function of distance from the shorting plate 64 at the feed end. The first null of the test fixture 58 is 90, the second null is 92, and so on to the last null 98 at the distal shorting plate 66. The distance between null 92 and null 94 is used to estimate half the guide wavelength as it would exist in the applicator 18.

Additional null-to-null values, e.g., 94 and 96, are used to establish that the desired mode has been stabilized, i.e. that the undesired evanescent modes are dampened over the distance or length used for the applicator 18. Lengths substantially less than one wavelength are not sufficient to accomplish the desired mode selection.

Furthermore, the specific absorption rate (SAR) produced at various depths in a bilayer phantom comprised of 1 cm of simulated fat and 10 cm of simulated muscle is improved as the guide wavelength is adjusted for the critical value. This feature is related to, but different from, the uniformity of transverse heating.

For example, at a given thickness of dielectric material 28 shaped as a taper in the feed region and uniform in the load region, the SARs are significantly lower than those produced by the same thickness in full length as shown in Table I.

TABLE I

| GUIDE HALF-WAVELENGTHS | $T_1$ | $T_2$ | $T_3$ | |
|---|---|---|---|---|
| 238 mm | 77 mW/g | 28 mW/g | 10 mW/g | tapered |
| 212 mm | 111 mW/g | 40 mW/g | 14 mW/g | 1.062" |
| 160 mm | 116 mW/g | 50 mW/g | 16 mW/g | +3/16" |

Notes:
All measurements are distance to node #3 minus distance to node #2 in 24" test fixture with electric field feed.

Location T1 was 12 mm below the fat-muscle interface. This distance is nearly 1/e depth; thus, the SAR at the interface is ca. 2.7 times higher or 208 mW/g for the longest guide wavelength and 313 mW/g for the near optimal guide wavelength. Since the net power was 50 W in all cases, the efficiency of the applicator is about 4 mW/g/Watt for the longest guide wavelength and about 6 mW/g/Watt for the near optimal case. This is a 50% increase in efficiency.

Lastly, the three sites of temperature measurement are 10 mm apart. In the case of the longest guide wavelength, the second site is 36% of the first site and the third site is 35% of the second site. In the case of the near optimal guide wavelength, the second site is 43% of the first site and the third site is 32% of the second site. This implies that the rate of attenuation with depth of propagation is improved with the near optimal guide wavelength for the bilayer fat/muscle model studied here.

The guide wavelength is adjusted by the use of low loss shims 41 to space the dielectric material 28 away from the wall until the critical guide wavelength is established and the SARs increase. The shims 41 must be thin because although the fields are low near the wall, excessive space prevents stable null-to-null distances.

Figure 12:
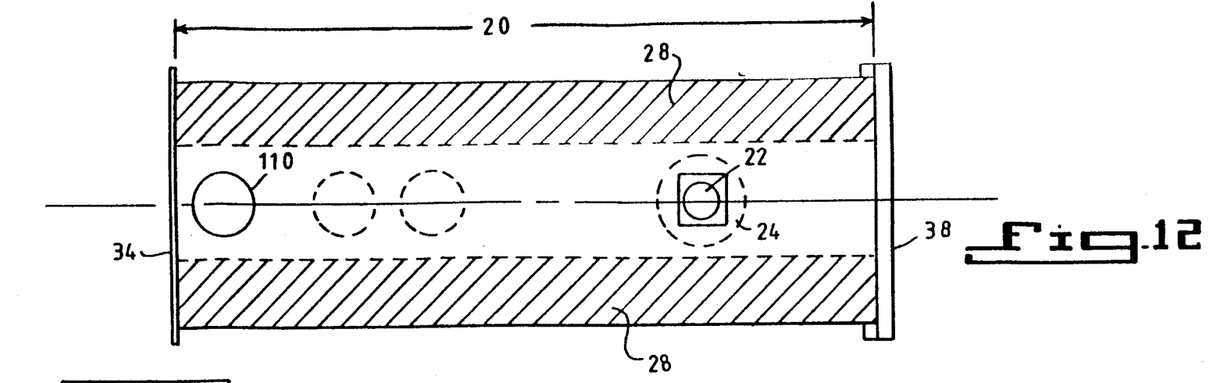
FIGS. 12 and 13 are analogous to FIGS. 1 and 2, respectively, with added functional block detail showing the method and apparatus for gas cooling and the means for suppression of RF leakage.
Figure 13:
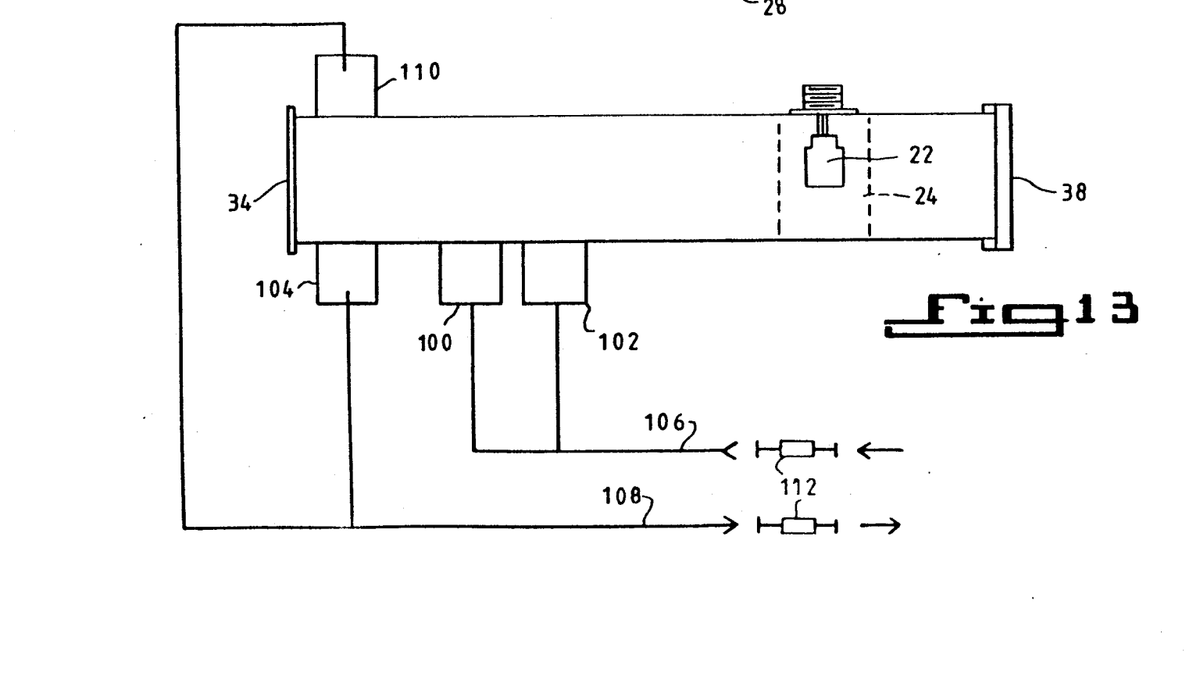

In FIGS. 12 and 13 the supply ducts 100 and 102 are waveguide below cut-off with attenuation of 60 db at the frequency of operation. They are connected by flexible hose 106 to a remote fan and source of air at a temperature not higher than 23 degrees C. FIGS. 12 and 13 demonstrate the method and apparatus for air cooling while maintaining contact with the patient and the means for suppression of RF leakage by the use of waveguide below cut off for cooling gas supply and return ducts.

The return ducts 104 and 110 are also wave guide below cut-off and connected to the low pressure side of the fan by flexible hose 108. The supply ducts 100 and 102 are located on one side to leave room for attachment of the applicator to a positioner. The air flow sensor(s) 112 is used to interrupt the power source via fault control 122 in order to not overheat the skin and superficial subcutaneous tissues in the event of fan failure.

Figures 14, 15:
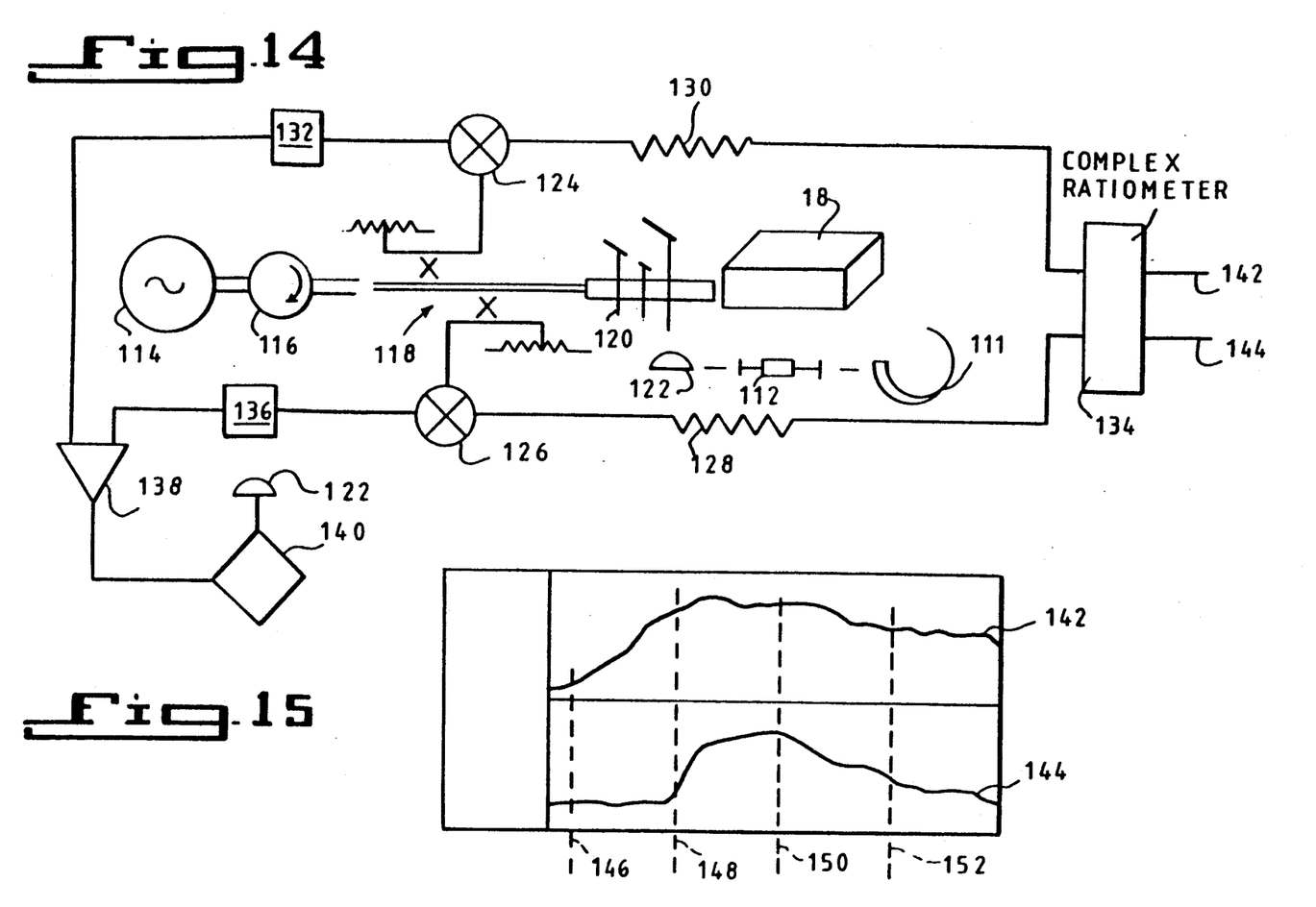
FIG. 14 shows a schematic functional block diagram of the system for the noninvasive detection of the therapeutic response, i.e., reactive hyperemia.
FIG. 15 is a graph showing changes in complex scattering parameter to moderate the therapeutic response for electromagnetic or nonelectromagnetic heating modalities.

FIG. 14 shows a system for detection of the individual therapeutic response and for treatment control. The method is based on changes in the wave impedance of muscle as its blood flow and blood content increase. The change in wave impedance of the muscle is detected by a change in the self impedance of the applicator measured at the terminals of the antenna, or at an integral number of half wavelengths from it, by means of a reflectometer and complex ratiometer. The onset of muscle blood flow is detected by a phase shift in applicator terminal impedance (toward the source) preceded by an increase of the reflection coefficient as the heating takes place.

The power source 114 is selected for frequency stability (1 part/ 1000 drift) and sufficient power output to produce SARs between 150 and 250 mW/g in bilayer fat/muscle phantoms using the applicator 18. Based on measurements in phantoms and human studies, 30 to 50 watts of CW power are needed. The power source is protected by a three port circulator 116 with a load to protect the power source should the applicator be operated when not matched to or in contact with the patient. The circulator output is connected to the main line of a dual directional coupler 118. The main line continues to a tuner 120, comprised of a stub and a line stretcher, then to the applicator/sensor 18. The air flow sensor 112, detects loss of air flow 111 to the applicator/sensor 18, and activates a fault control 122 to interrupt the power source.

The forward and reverse coupled arms are connected to separate power dividers 124 and 126. Attenuation to power levels appropriate for the subsequent instrumentation is accomplished by separate attenuators 128 and 130. When divided, the forward coupled arm enters a bolometer mount, or other power sensor, to measure the forward power via the meter 132.

The other half becomes the reference signal for a complex ratiometer 134. The reverse coupled arm after power division is sampled by the reverse power meter 136 and becomes the test channel for the complex ratiometer 134. The forward and reverse powers, 132 and 136, are subtracted in the differential amplifier 138 and displayed by the dosimeter 140 as the net absorbed energy per unit time. Failure to maintain the selected net absorbed energy per unit time also activates the fault control 122 to interrupt the power source. Net absorbed power is used, therefore, for three purposes: (1) to assist regulation of the net energy per unit time delivered to the patient; (2) to establish a very good match to the patient at the baseline power level; and (3) to detect coupling faults.

Tests have shown that a return loss of 30 dB or better is advantageous. Similarly, the directivity of the reflectometer tuner 120 should be 40 dB or better. The tuner 120 is adjusted to maximize the ratio of forward to reverse power by a procedure well known to those skilled in the art. The complex ratiometer produces two output signals as functions of time as shown in FIG. 15, the magnitude 142 and phase 144 of power wave scattering parameter $S_{11}$.

With reference to FIG. 14, if another form of heating is used, such as ultrasound, the sensor functions may still be implemented. The changes in the instrumentation block diagram are to replace the high power generator 114, with a low power source at the same frequency, and to reduce the value of attenuation in attenuators 128 and 130 to be appropriate for the complex ratiometer 134 input levels. For example, the high power source of 30 to 50 watts would be reduced by 30 dB and the attenuators 128 and 130 would be changed for 30 dB less attenuation in order to set proper signal levels at the complex ratiometer 134.

With reference to the complex ratiometer outputs shown in FIG. 15, the time curse of the complex scattering parameter discloses biophysical events in the muscle by virtue of the effect of changes in the wave impedance due to the blood flow and blood content of that tissue. Since the applicator/sensor 18 is closely coupled to the tissue being heated, the self impedance of the applicator is effected by the change in wave impedance in the tissue as the blood flow and blood content increase.

The change in applicator/sensor self impedance is monitored at the antenna's terminals, or at an integral number of half wavelengths toward the generator, by changes in the complex reflection coefficient as normalized by the forward wave.

Furthermore, in reference to the complex ratiometer outputs 142 and 144 shown in FIGS. 14 and 15, the observed changes in the magnitude of $S_{11}$ recorded over time as in 142 are a gradual increase in the magnitude, without a significant change in phase, as the tissues heat. These events are illustrated at time reference 146 when the specified net energy per unit time is first established. The latency, time at 148 minus time at 146, to onset of phase shift 144 is shown in rectangular coordinates by indicator 134. The end of power application is shown at 150 and start of the range of motion/strength exercises during the cool-down period at 152 is also shown in FIG. 15.

In terms of a polar display of $S_{11}$, the magnitude increases substantially along a radius of constant phase. As the change of magnitude approaches a plateau, a latency of several minutes, shown at 146 and 148, is required before the phase rotates toward the generator on the Smith chart.

This phase rotation often takes place coincident with a reduction in the subjective feeling of deep heat. This sequence of events typically takes 10 to 20 minutes at the stated reference SARs. The latency, time at 148 minus time at 146, corresponds to the time necessary to elevate muscle temperatures to the point where local vasodilation takes place. At that point, the phase rotation takes place with characteristically small additional changes in magnitude.

Figure 16:
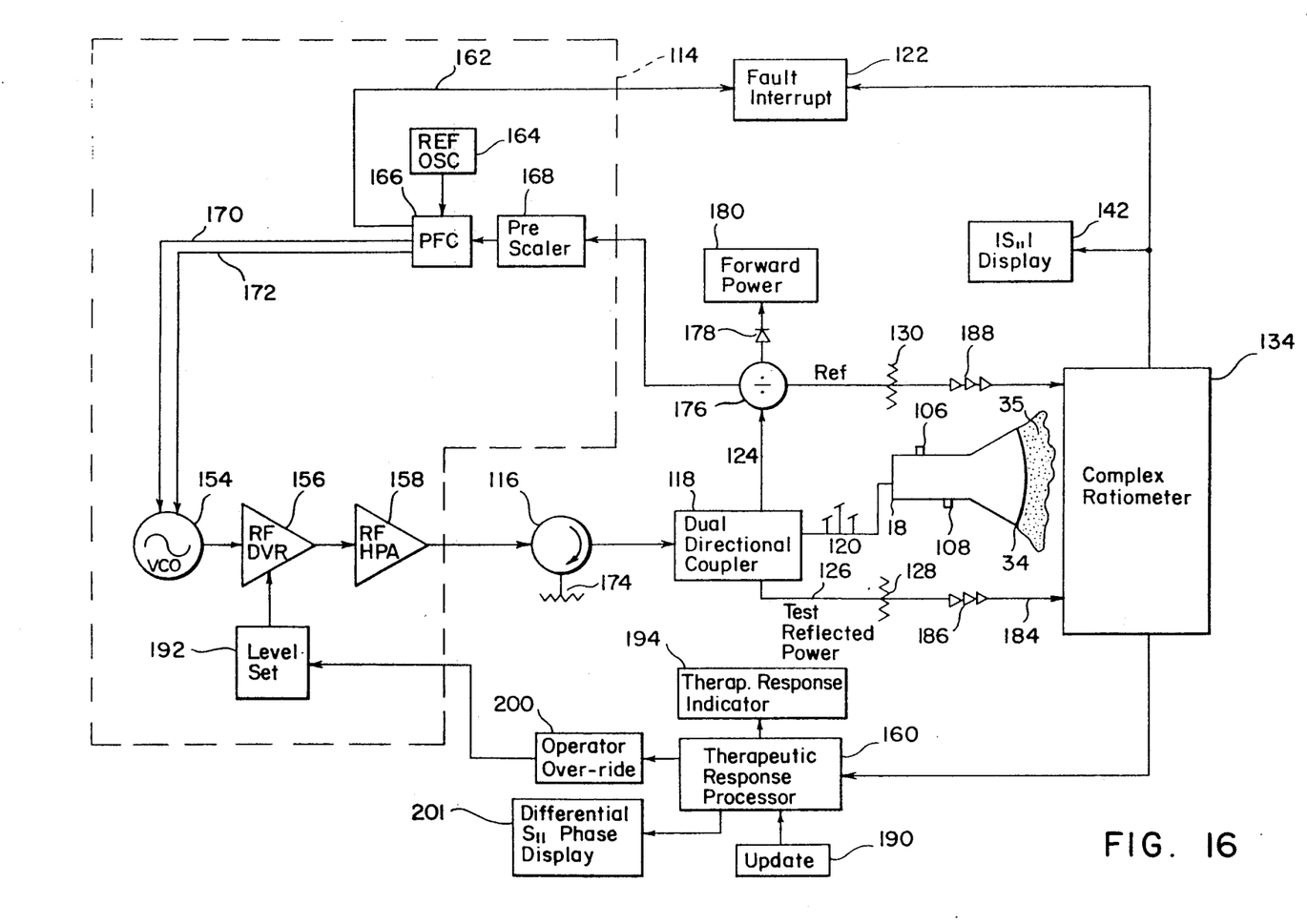
FIG. 16 is a block diagram illustrating the stabilized power source used in the apparatus of the invention.

FIG. 16 is a system block diagram illustrating a stabilized master-oscillator power-amplifier RF source 114 with electrical control of drive level. The power source 114 includes a stabilized master oscillator 154, a driver amplifier 156, and a power amplifier 158. Stabilization of the oscillator is necessary to limit short term drift to not exceed 0.1% of the carrier frequency per minute. This drift specification must be consistent with the reset period in the subsequent therapeutic response processor 160, as detailed in the discussion of FIG. 18. The frequency drift specification is consistent with cavity stabilization, but a phase locked loop (PLL) is the preferred embodiment. PLL is advantageous as a loss-of-lock output 162 is available to the fault interrupt 122, thereby preventing misinterpretation of short term oscillator drift as a therapeutic response. The preferred embodiment of the RF master oscillator is a voltage controlled RF oscillator 154 stabilized by a reference oscillator 164 and phase frequency comparator (PFC) 166 preceded by a prescaler, 168 to compare the output frequency with the reference frequency in the PFC. The PFC outputs provide the voltage control to VCO 154 via up and down command voltages 170 and 172, respectively, in a servoloop as is well known to those skilled in the art of PLL applications.

Air cooling of applicator 18, via chilled air supply duct 106 and return duct 108, serves to remove heat from the skin and subcutaneous tissues being heated. This is accomplished via thermal conduction through radome 34 down the thermal gradient between the applicator and skin 35 with which it is closely coupled. Failure of air cooling activates fault interrupt 122.

The power amplifier 158 is protected from excessive reflected power by circulator 116 and external load 174. Initial match of the contact-type applicator/sensor 18 coupled to the treatment site 35 is established by means of manually adjustable tuner 120, in combination with the displayed value of return loss 142. The initial match so produced (ca −20 dB) is not subsequently adjusted unless it is necessary to reposition the applicator. Dual directional coupler 118 provides samples of the forward 124 and reflected 126 power. The sample of forward power is operatively connected to a 3-way power divider 176 to provide for oscillator phase lock and to provide for forward power display by detector 178 and meter 180; and to provide for forward power input 182 to the reference channel of the complex ratiometer 143. The reflected (test channel) power 126 is also input 184 to the complex ratiometer 134 comprising the test channel. The maximum power levels input to the complex ratiometer 134 are set by attenuators 128 and 130 for test and reference ports, respectively. These input ports are further buffered by constant phase, limiting amplifiers 186, 188 respectively. Typical limited values for the reference channel are +10 dBm; whereas levels of 0 dBm are needed on the test port in order to minimize errors in phase estimation due to mixer conversion effects and AM to PM conversion.

Estimation of a baseline phase of $S_{11}$ (against which later measurements are compared during heating) is automatically entered into the therapeutic response processor 160 at start-up or at any time memory update is selected by 190 as detailed in FIG. 18. Detection of therapeutic response reduces the RF drive level by operative connection to RF level control 192, activates a therapeutic response indicator 194 and ends the treatment session, unless that feature is over-ridden, 200, by the operator. The phase differential of $S_{11}$ is indicated on a display 201.

Figure 17:
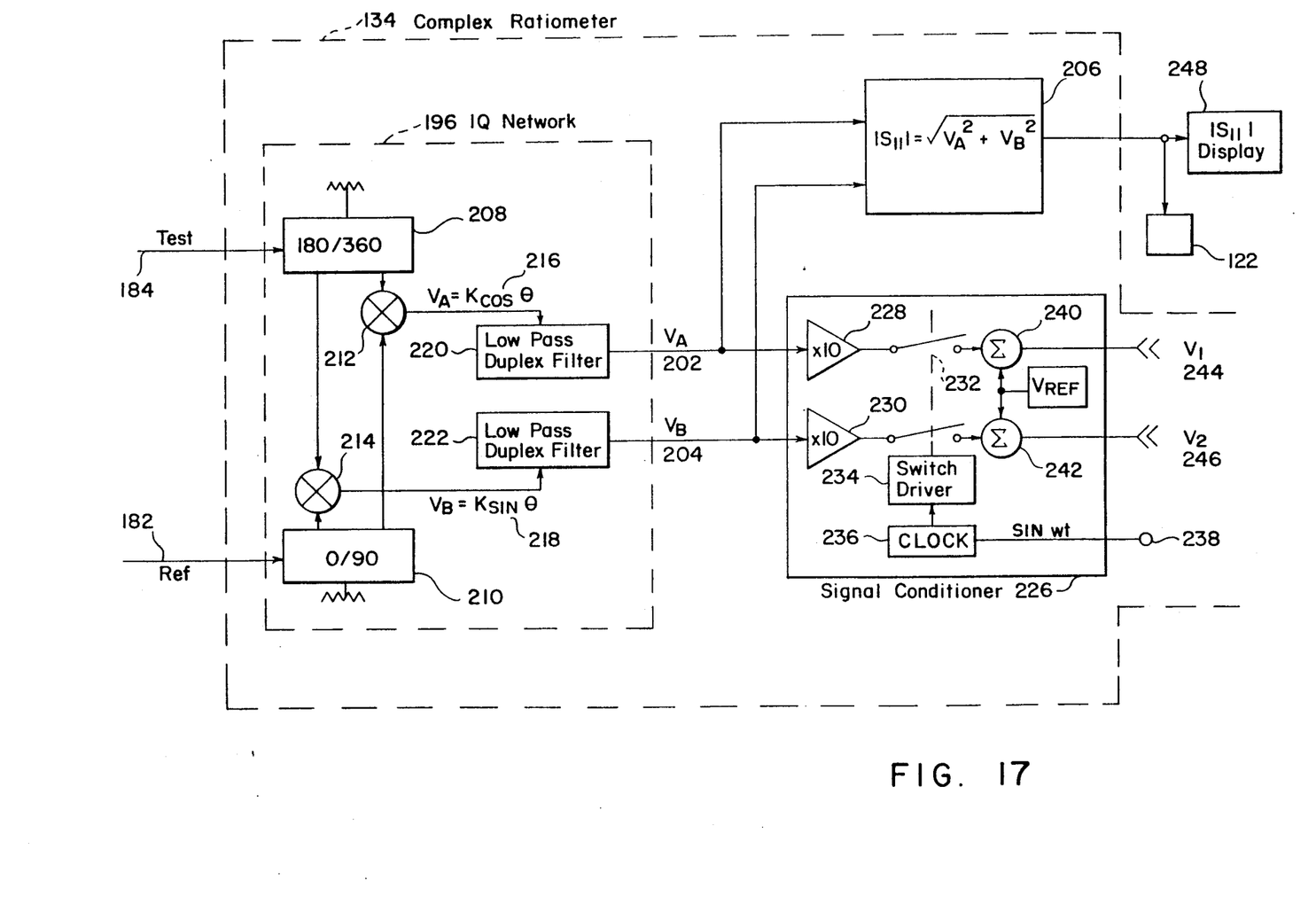
FIG. 17 is a block diagram showing in detail the ratiometer of the invention.

Referring now to FIG. 17, the complex ratiometer 134 is shown in more detail. The samples of forward and reflected power are inputs whereas the magnitude and phase of $S_{11}$ are outputs. The preferred embodiment of the complex ratiometer takes samples of the forward and reflected power 182 and 184, respectively, as inputs to the in-phase in-quadrature (IQ) network 196. Two outputs, $V_a$ and $V_b$, 202 and 204, respectively, are produced that represent the sine and cosine of the phase angle between the forward and reverse power waves. These two outputs of the IQ network become inputs to a magnitude computer 206 to produce the magnitude of $S_{11}$, 142 and become input to a phase computer to produce the phase 144 of $S_{11}$. The former is not described here as this can be implemented by conventional circuits well known to those skilled in the art of signal processing.

The preferred embodiment of the IQ network 196 is based on transmission line couplers integrated with matched diode bridges. One hybrid is a sum/difference RF hybrid 208; the other is a quadrature RF hybrid 210. The unused ports of the hybrids are terminated by matched loads. The reference signal 182 is input to the quadrature hybrid 210 whereas the test signal 184 (reflected power) is input to the sum/difference hybrid 208. The two double balanced mixers 212 and 214 provide DC coupled IF outputs proportional to the cos of $\theta$ 216 and sine of $\theta$ 218, buffered by duplex filters 220 and 222, respectively, to prevent spurious mixer responses due to IF port mismatch at the RF/LO frequency.

The preferred embodiment of the phase computer is a tracking converter 224 (FIG. 18) preceded by a signal conditioner 226. The signal conditioner serves two purposes: amplification with appropriate loading to the diodes of the IQ network outputs; and modulation of a carrier frequency by the IQ outputs for later processing by a tracking ratiometric converter. Buffering and voltage scaling is provided by input amplifiers 228 and 230 for $V_a$ and $V_b$, respectively. Typical values for the input impedance of the amplifiers, for use with the IQ network, are 5 kilo-ohms. Typical gain is 10. These scaled values are modulated with a MOSFET double throw double pole switch 232 with a switch driver 234 and 1 KHz square wave from clock 236 that also provides an output 238 to the subsequent ratiometric converter. This clock output 238 is needed to provide a reference carrier frequency for later synchronous detection within the ratiometric converter. The modulated carrier is summed via operational summers 240 and 242, respectively, with a reference voltage to become outputs $V_1$ and $V_2$. The modulated and level shifted version of outputs of the IQ network, denoted as $V_1$ and $V_2$ and labeled as 244 and 246, respectively, become inputs to the ratiometric, tracking converter shown on drawing 18. The IQ network outputs, Va and Vb, are also used by the magnitude calculator 206, which implements the square root of the sum of squares of $V_a$ and $V_b$ to yield the magnitude of $S_{11}$, 142. This is displayed by 248, as an aid to initial tuning by use of tuner 120 to reach return loss of ca. 20 dB. It is also input to fault interrupt 122 to stop power delivery under conditions such as loss of contact of the applicator from the patient.

Part of the ratiometer 134 is a digital, tracking ratiometric converter based on a Type II servoloop. This provides fresh digital, phase data with no more than 1 LSB error to the therapeutic response computer. Ratiometric processing obviates the need for a signal conditioner free of drift. The only requirement is that the two channels are effected similarly.

The preferred embodiment of the phase computer is a type II tracking converter preceded by a signal conditioner to scale the inputs and provide a carrier frequency modulated by the $V_a$ and $V_b$ as previously described in FIG. 17. The tracking converter 224 is shown in FIG. 18 and begins with multiplication of the inputs $V_1$ and $V_2$, i.e. 202 and 204 by a trigonometric generator 250 with sine 252 and cosine 254 outputs (the latter derived by a 90 degree phase shift 256) that multiply each $V_1$ and $V_2$ by the cosine and sine of an estimated angle $\phi$ from up/down counter 258. The trig generator 250 is a multiplying DAC operatively connected to the up-down counter 258 embedded in a type two servo loop comprising a difference calculator 260, a synchronous detector, i.e. demodulator 262, plus low pass filter 264 to a voltage-to-frequency converter 266. The rate is proportional to the difference of the data and the estimated angle φ from 250, while the sign or count direction is determined by the sign of the difference between θ and φ. This up/down counter 258, therefore, responds to both the sign and magnitude of the difference between θ (data) and φ (estimated) and is fed back to the trig generator DAC 250 and also loads latches 268 that interface the output, i.e. φ 144 of the tracking converter to the therapeutic response processor 160. The latches are not updated during changes in the input data. The loop servos the difference between θ and φ to 'zero', i.e. 1 LSB on a radian binary scale, according to well known principles of Type two servo loops and trigonometric identities. The ratiometric processor tracks the input data, neutralizes common mode disturbances, and supplies a fresh digital representation, except for updates, of θ to the output pins within the bandwidth of the servo loop. The loop bandwidth must be large enough to track changes in θ as the treatment site is heated. Based on clinical trails, it would appear that a loop band width of 100 Hz is easily fast enough to track θ in this application.

The value of the phase angle 144 becomes input to the therapeutic response processor 160. This is a processor for detection of a threshold in the first derivative of a smoothed version of the time rate of change of phase angle during heating. The preferred embodiment of the therapeutic response processor 160 is a time normalized, differential angle computer which outputs the difference of a resettable reference phase angle stored in register A 270 (i.e. the baseline phase angle), and an instant value of θ stored in register B 272. These are transferred to the register outputs, and thence to the inputs of full adder (FA) 274, configured to subtract A from B, upon each occurrence of a clock pulse to each separate resister. In the absence of clock pulses, the data is not transferred from register inputs to the register outputs; thus, prior data remains in the outputs.

Figure 18:
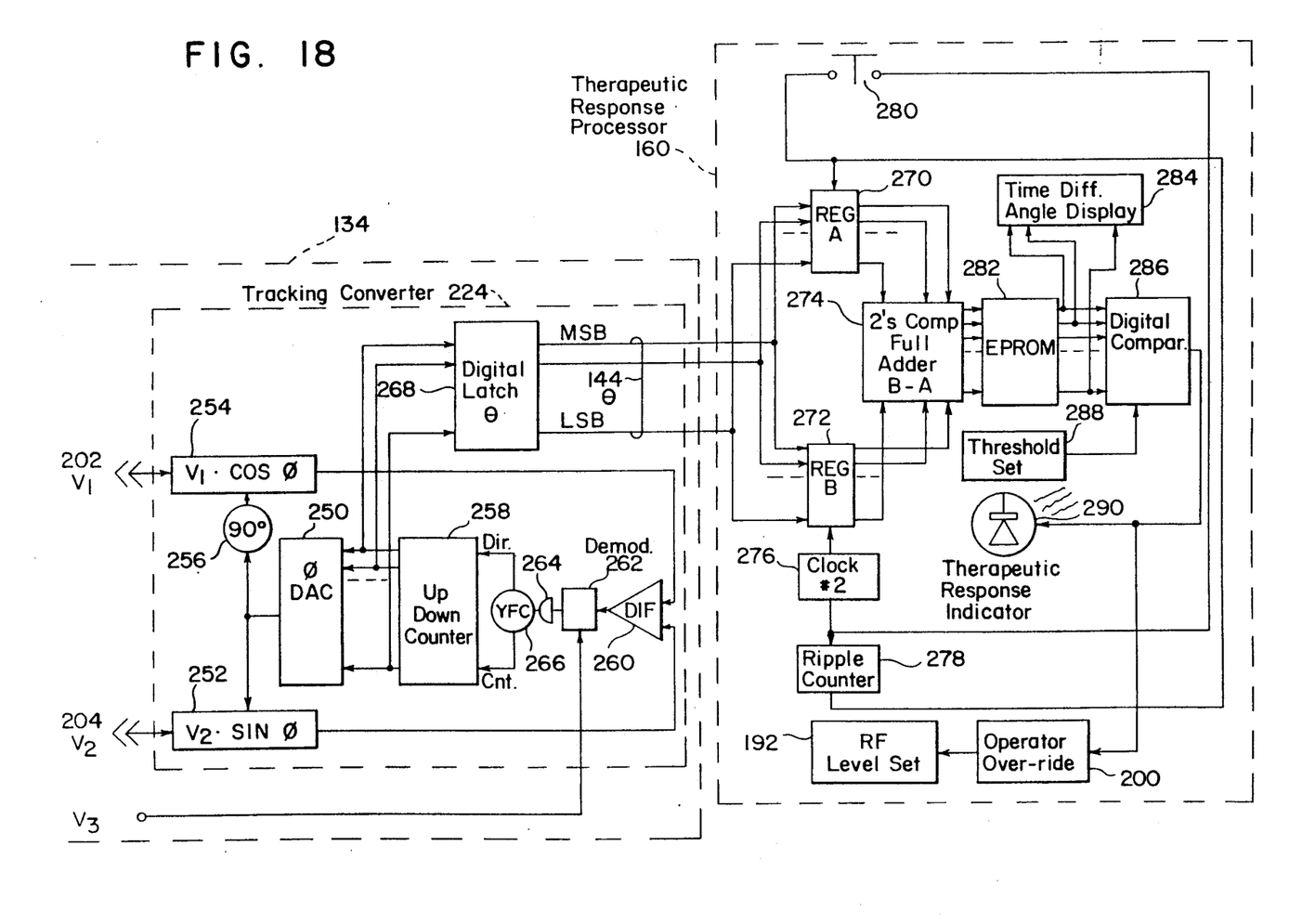
FIG. 18 is a block diagram of a portion of the ratiometer and of the therapeutic response processor of the invention.

With respect to FIG. 18, the parallel binary outputs of registers A and B 270 and 271 are in radian base as derived from the tracking converter. A difference is formed between a reference and an instant value of θ in the parallel binary (radian base) output of adder 274. At start-up of the processor, these are identical; but the instant register B is updated with each pulse from clock 276 whereas the reference register A is not updated until a preset number of clock pulses have occurred as determined by ripple counter 278. An output from the ripple counter is the clock pulse to register B. At that time, both registers contain identical data. This resetting action takes place approximately once per minute in order to prevent long term drift appearing to be a therapeutic response. Clock 276 outputs a pulse rate to the B register at 1 to 10 Hz insofar as the change in phase angle with heating is rather slow. The processor may also be updated manually by making contact with switch 280 to accommodate shift in patient position, and/or re-adjustment of tuner 70, for example.

The output of the differential angle processor is an absolute value of the difference of the instant and the stored values of the phase angle of $S_{11}$ in radian base, parallel binary form. An EPROM 282 serves to convert the radian base, differential angle into a parallel binary, base two number. EPROM 282 operates as a look-up table and applies calibration data for the IQ network. The base two, parallel binary difference (i.e. the differential phase angle) is continuously displayed on a 7 bit, 102 segment, bar graph meter 284.

The EPROM output also becomes input to a threshold logic unit (TLU). The preferred embodiment of the TLU is digital comparator 286 with threshold set 288. The threshold value, 61, has been determined from clinical tests to be 10–20 degrees of differential phase shift within any one minute interval after initial heating has occurred. The output of TLU is used to energize a therapeutic response indicator 290. It may also end the treatment session by means of the RF power level set 192 unless this feature is disabled, via override 200, by the operator.

In operation, the complex ratiometer provides estimates of the phase and magnitude of the reflected power wave before and during heating. The phase angle of scattering parameter $S_{11}$ is monitored during heating for a threshold in its time normalized difference from initial conditions by a resettable threshold comparitor to indicate occurrence of the therapeutic response. This event will stop the treatment session, unless that feature is disabled by over-ride 62. Parameters displayed are the forward power, the reflected power differential phase angle, and the return loss.

The in-phase in-quadrature (IQ) network provides DC voltage outputs proportional to the sine and cosine of the phase angle θ between the forward and reflected power waves. These outputs of the IQ network become inputs to a signal conditioner that modulates a carrier frequency by the two levels prior to calculation of the phase of $S_{11}$. The IQ network also provides these outputs to a processor for the magnitude of complex scattering parameter $S_{11}$. The magnitude output is used to aid operation of the tuner to establish the initial match, and it is used to activate a fault interrupt if the applicator loses contact with the treatment site.

Therapeutic response detection is based on the time rate of change of the phase angle of the reflected power wave, in comparison to initial or reset phase angle, as the treatment site is heated by the contact applicator/sensor. The absolute phase of $S_{11}$ is not of interest; thus, the effect of the static phase shift due, e.g., to power divider in the forward arm is of no consequence for this use.

Figure 19:
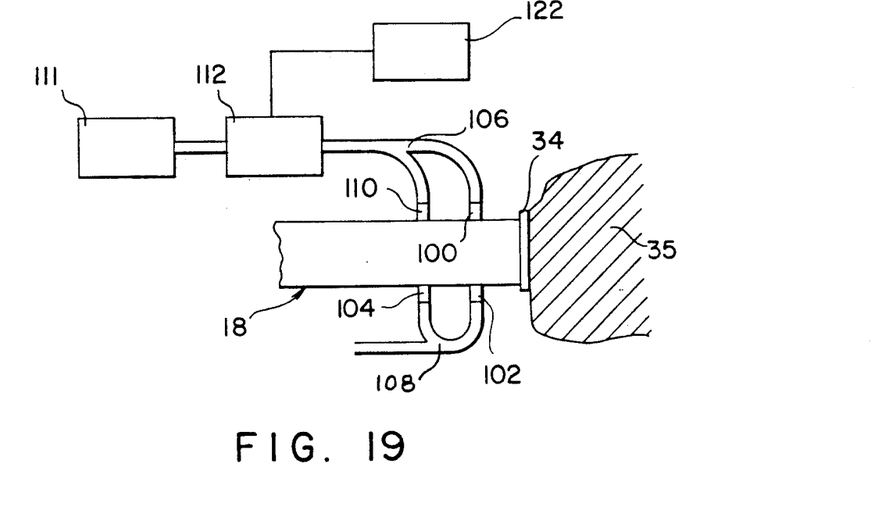
FIG. 19 is a system diagram of the applicator with the radome in contact with a treatment site.
Figure 20:
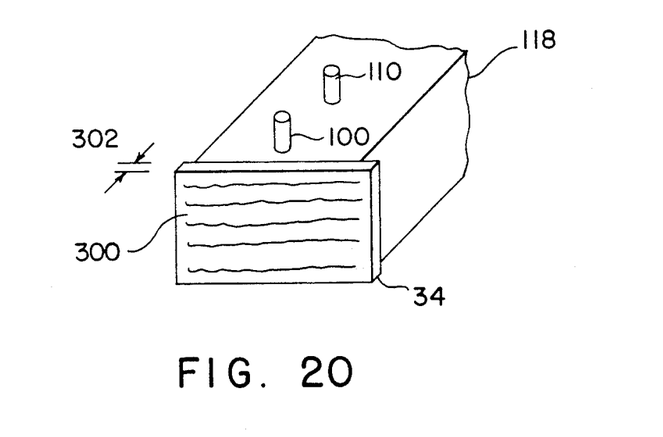
FIG. 20 is a perspective end view of the application with the radome.
Figure 21:
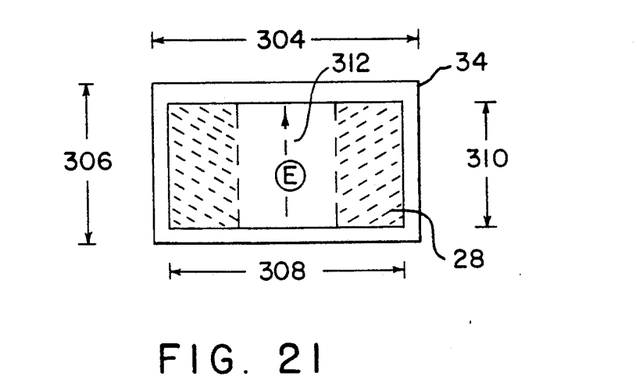
FIG. 21 is an elevation view of the applicator from the proximal end thereof.

Turning now to FIGS. 19–21, the improved radome according to the invention will be described. FIG. 19 shows the waveguide applicator 18 having a radome 34 in contact with a treatment site 35. The supply and return hoses 106 and 108, respectively, carry the chilled air from refrigeration unit 111 to ducts 110, 100 and 104, 102 configured as waveguides below cut-off for the frequency of operation of the electromagnetic diathermy source. An air flow detection switch 112 activates the fault interrupt 122 if air flow drops below 50 cfm.

FIG. 20 shows the radome 34 comprised of composite material, preferably glass-reinforced plastic, where the dielectric constant at the frequency of operation is in the range k'=3 to 5, and the reinforcement fibers 300 are cross-polarized to the electric field. The thickness 302 of the radome is a small fraction (1/100) of a wavelength in free space. In the preferred embodiment, the frequency of operation is 915 MHz and the free space wavelength is 12" whereas the thickness of the radome is 0.030".

FIG. 21 shows that the outer extent 304, 306 of the radome must extend beyond the transverse dimensions 308, 310 of the applicator by at least ¼" at the preferred frequency of operation, but most important is the need to cover waveguide walls parallel to the electric field 312 to prevent fringe field heating.

The radome is a thermal interface between heat sources induced at the treatment site and the heat sink provided by cooling the entire applicator. There is a thermal gradient across the radome. The radome not only covers the aperture, but is the heat conduction path between the heat sources in the treatment site and the heat sink produced in the applicator.

Figure 22:
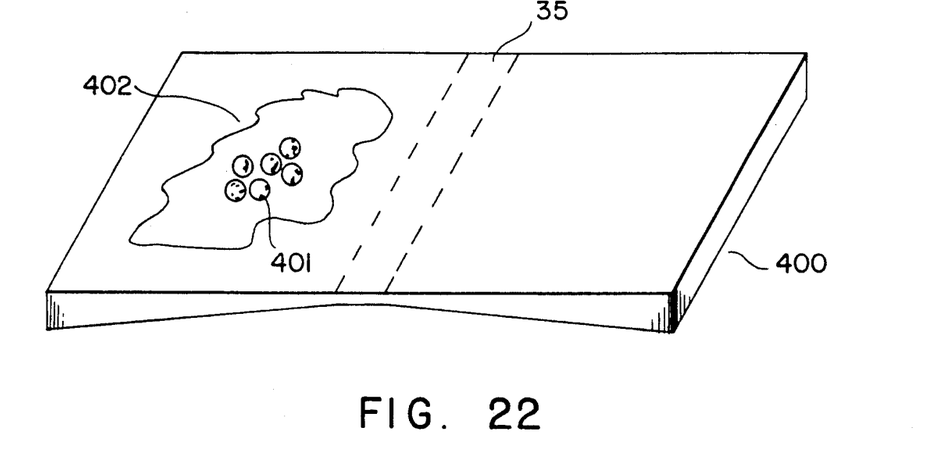
FIG. 22 and 23 are perspective views of the bolus according to the invention.

The improved bolus according to the invention will be described with reference to FIGS. 22-24. FIG. 22 shows the bolus 400 comprised of ceramic spheres 401 composed of high purity (ca 98%) $Al_2O_3$ constrained in an elastic pouch 402. When packed in a knit pouch, the final relative dielectric constant is in the range $k'=3$ to 5. This approximates the dielectric constant of fat/skin to reduce scattered fields. The high purity ceramic is needed to reach a high dielectric constant of 9.8 and a low loss tangent of not more than 0.005 for the spheres.

Figure 23:
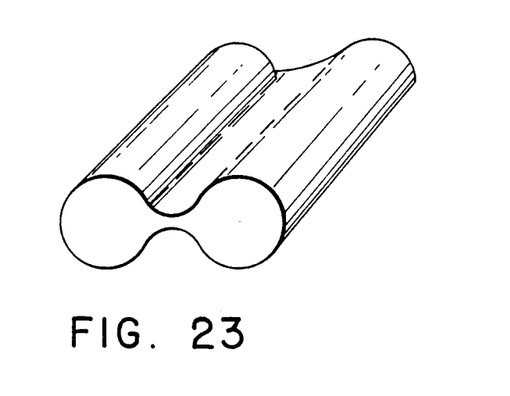

FIG. 23 shows the bolus 400 shaped to conform to the treatment site 35. The size and disposition of spheres in the bolus bag is altered to accommodate a canonical set of surface conditions: saddle bags for cylindrical extremities, wedges for sloped regions, toroids for bony protuberances.

Figure 24:
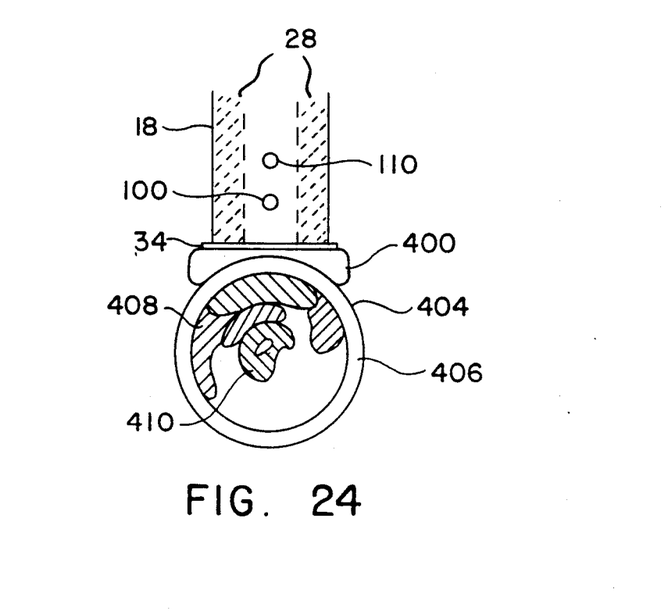
FIG. 24 is a sectional view of the apparatus applied to a treatment site via the bolus of FIGS. 22 and 23.

As shown in FIG. 24, the bolus is arranged between the applicator 18 and the treatment site, 35, in such a way that the central, air filled, portion of the aperture has a minimum bolus. The majority of bolus material is preferably disposed to the lateral extent of the aperture where the dielectric blocks 28 end at the radome 34. Waveguide below cut-off ducts 100 and 110 are shown near the radome 34. The treatment area comprises an outer layer of skin 404 surrounding a fat layer 406 within which the muscle 408 and bone 410 are contained.

Whereas certain specific embodiments of the improved method and apparatus for deep heat treatment of musculoskeletal disorders have been disclosed in the foregoing description, it will be understood that various modifications within the scope of the invention may occur to those skilled in the art.

Therefore, it is intended that adaptations and modifications should be comprehended within the meaning and range of functional equivalents of the preferred embodiments. For example, changes in material and dimensions that are subsumed in the teaching of the instant patent may be used in place.

Likewise the display options for detection of the therapeutic response may use any of the equivalent parameters of impedance, reflection coefficient, scattering parameter $S_{11}$, or admittance displayed in rectangular or equivalent polar co-ordinates or co-ordinate transformations such as the Smith chart or Carter chart.

Similarly broader bandwidth (10% to 20%) impedance matching may be employed to augment the narrowband reactive tuner as is well known to those skilled in the art.

What is claimed is:

1. A deep heat treatment musculoskeletal apparatus for detection of therapeutic response and treatment control based upon change in the wave impedance of tissue as tissue blood flow and blood content change, comprising
   (a) a stabilized power source of radio frequency power;
   (b) a combined radio-frequency waveguide applicator and sensor connected with said stabilized power source and adapted for close coupling to the tissue;
   (c) a dual directional coupler connected with said stabilized power source and with said applicator and sensor; and
   (d) a complex ratiometer connected with said coupler for indicating phase and magnitude of a complex scattering parameter as a function of time over an interval of deep heat treatment, said scattering parameter resulting from changes in wave impedance due to blood flow and blood content of the tissue being heated;
   (e) means for comparing an instantaneous phase and magnitude value of said scattering parameter with a reference value; and
   (f) means for indicating when said instantaneous value of said scattering parameter crosses a threshold relative to said reference value, thereby to provide an indication of therapeutic response.

2. Apparatus as defined in claim 1, wherein said stabilized power source comprises a master oscillator stabilized to limit frequency drift over the duration of deep heat treatment.

3. Apparatus as defined in claim 2, wherein said stabilized power source further comprises amplifier means connected with said master oscillator for amplifying the output thereof.

4. Apparatus as defined in claim 2, wherein said ratiometer includes an in-phase in-quadrature network for receiving power signals corresponding with the power supplied to the tissue and with scattered power reflected therefrom, said network producing outputs proportional to the phase angle between said power signals.

5. Apparatus as defined in claim 4, wherein said complex ratiometer includes a signal conditioner for amplifying and modulating said network outputs and a tracking, ratiometric converter for tracking the phase angle.

6. Apparatus as defined in claim 2, and further comprising a therapeutic response processor connected with said ratiometer for detecting the time rate of change of phase angle during therapeutic treatment of the tissue.

7. Apparatus as defined in claim 6, wherein said processor includes a differential angle processor which produces an output which is an absolute value of the difference between instant and stored values of the phase angle of the scattering parameter in radian base, parallel binary form.

8. Apparatus as defined in claim 7, wherein said processor further comprises memory means for converting the phase angle into a base two number and display means for displaying said phase difference.

9. Apparatus as defined in claim 8, wherein said processor further comprises a threshold logic means for energizing a therapeutic response indicator when said phase difference reaches a predetermined value.

* * * * *